United States Patent [19]

Hunt et al.

[11] Patent Number: 4,583,396
[45] Date of Patent: Apr. 22, 1986

[54] CONTAMINATION LEVEL INDICATOR

[75] Inventors: Trevor M. Hunt, Bristol; Desmond E. Bowns, Bath, both of England

[73] Assignee: Ministry of Defence, London, England

[21] Appl. No.: 604,650

[22] PCT Filed: Aug. 4, 1983

[86] PCT No.: PCT/GB83/00194

§ 371 Date: Apr. 11, 1984

§ 102(e) Date: Apr. 11, 1984

[87] PCT Pub. No.: WO84/00816

PCT Pub. Date: Mar. 1, 1984

[30] Foreign Application Priority Data

Aug. 13, 1982 [GB] United Kingdom ............... 8223402

[51] Int. Cl.⁴ ............................................ G01N 15/06
[52] U.S. Cl. ................................................. 73/61 R
[58] Field of Search .............. 73/61 R, 61.1 R, 53, 73/54, 61.4; 340/627

[56] References Cited

U.S. PATENT DOCUMENTS

| | | | |
|---|---|---|---|
| 3,111,839 | 11/1963 | Evans et al. | 73/61 R |
| 3,266,299 | 8/1966 | Swank | 73/61 R |
| 3,271,999 | 9/1966 | Dwyer et al. | 73/61 R |
| 3,357,236 | 12/1967 | Kasten | 73/61 R |
| 3,452,586 | 7/1969 | Childs et al. | 73/61 R |
| 3,499,315 | 3/1970 | Marino | 73/61 R |
| 3,678,881 | 7/1972 | Shinn | 73/53 |
| 3,686,926 | 8/1972 | Miller et al. | 73/61 R |
| 3,893,334 | 7/1975 | Williams | 73/61 R |
| 3,900,290 | 8/1975 | Hornstra | 73/61 R |
| 4,495,799 | 1/1985 | Fisher et al. | 73/61 R |

FOREIGN PATENT DOCUMENTS

2102768 7/1972 France .
1098186 1/1968 United Kingdom ............... 73/61 R

*Primary Examiner*—Stewart J. Levy
*Assistant Examiner*—Hezron E. Williams
*Attorney, Agent, or Firm*—Cushman, Darby & Cushman

[57] ABSTRACT

Apparatus for providing an indication of the level of contaminant in a fluid includes a pervious barrier (12) disposed across a fluid path (11) so that the barrier (12) will be progressively blocked by contaminant in the fluid. Monitoring means responsive to the rate of blocking of the barrier provides an indication of the level of contaminant in the fluid. The monitoring means may be means for sensing measurements representing the rate at which the pressure of the fluid upstream of the barrier (12) rises. Alternatively the monitering means senses measurements representing the rate at which the flow rate of fluid through the barrier (12) falls. The provision of an indication conveniently completes a measurement cycle and there is means for renewing the barrier, either by back-flushing the barrier (12) or alternatively by exchanging one barrier for another.

14 Claims, 8 Drawing Figures

CONTAMINATION LEVEL INDICATOR

FIELD OF THE INVENTION

This invention relates to apparatus for obtaining an indication of the quantity of non-soluble contaminant in a fluid. In the context of this specification the term "contaminant" is defined to include any undissolved substance present in a fluid whether or not its presence therein is intended.

BACKGROUND OF THE INVENTION

In many systems using fluids it is important to know the level of non-soluble contamination in the fluid, either because the contaminant will damage the system and/or because the presence of contaminant indicates wear or breakdown in the system. In other fluids it is desirable to maintain the level of particulate material therein at an approved or known value. Present methods of automatically monitoring the level of contaminant involve expensive and complicated equipment and in most cases the tests can only be performed by highly trained personnel. It is an object of this invention to provide an apparatus which can give an indication of such contamination in a simple and speedy manner.

SUMMARY OF THE INVENTION

From one aspect the invention relates to an apparatus for providing an indication of the level of contaminant in a fluid, comprising means for defining a fluid path along which the fluid may be caused to flow, a pervious barrier disposed across the fluid path so that the barrier will be progressively blocked by the contaminant as the fluid flows through the barrier, and monitoring means responsive to the rate of blocking of the barrier, thereby to provide an indication of the level of contaminant in the fluid.

The monitoring means may comprise flow rate control means adapted to maintain constant the flow of fluid supplied to the barrier, and pressure rate sensing means for sensing measurements representing the rate at which the pressure of the fluid upstream of the barrier rises. The pressure rate sensing means conveniently comprises timing means and pressure sensing means to sense the pressure of the fluid upstream of the barrier.

In one arrangement the timing means is adapted to indicate the elapse of a predetermined time period and the pressure sensing means senses the pressure of the fluid at the end of said elapsed time period. Alternatively the pressure sensing means is adapted to sense when the pressure of the fluid reaches a predetermined value, and the timing means measures the time taken for the pressure to reach said predetermined value.

In another arrangement the monitoring means comprises pressure control means adapted to maintain constant the pressure of fluid supplied to the barrier, and flow rate sensing means for sensing measurements representing the rate at which the flow rate of fluid through the barrier falls. The flow rate sensing means conveniently comprises timing means, and flow rate measuring means to measure the flow rate of the fluid through the barrier.

In this case the timing means is conveniently adapted to indicate the elapse of a predetermined time period, and the flow rate measuring means measures the flow rate of the fluid at the end of said elapsed time period. Alternatively the flow rate measuring means is adapted to detect when the flow rate of the fluid drops to a predetermined level, and the timing means measures the time taken for the flow rate to fall to said predetermined level.

In a preferred embodiment the provision of an indication completes a measurement cycle and the apparatus further comprises barrier renewal means for renewing the barrier at the end of each cycle. The barrier renewal means may reverse the flow in the fluid path for a sufficient time to back flush the barrier and then return the flow to its original direction whereafter a further measurement cycle can occur. In this case the barrier renewal means may flush the fluid path before initiating the further measurement cycle. Alternatively the barrier renewal means may reverse the flow in the fluid path to initiate a new measurement cycle at the reversal or a predetermined time thereafter.

A series of barriers may be provided on a carousel, a movable strip or frame, such that a new barrier can be introduced into the fluid path at the end of each cycle or set number of cycles or set time to initiate a new cycle or cycles or time. Alternatively the barrier may be reversed at the end of each measurement cycle.

The apparatus may further include averaging means for providing a mean of the indications over a plurality of cycles.

The barrier may be constituted by a perforate screen, membrane, filter, mesh, grid or other pervious barrier. For example, the barrier may be a woven metal grid. The pore or aperture size of the barrier will be similar to the size of contaminant particle it is intended to trap, for example, in fluid power hydraulic systems it may be between 1 and 200 microns.

Preferably the fluid path of the apparatus is connected or connectable in parallel with a working fluid system to sample fluid from the system. The cross-section of the fluid path is conveniently much less than that of the fluid system adjacent the path. Alternatively the fluid path of the apparatus is connectable to a container containing a sample of fluid taken from a fluid system.

The apparatus may include a range of grades of barrier, typically two—coarse and fine—and means for disposing one or another in the fluid path.

In another alternative embodiment the barrier is movably mounted in the fluid path such that the barrier can be moved by the fluid as the barrier becomes progressively blocked with contaminant, and there is provided means for monitoring the movement of the barrier to provide an indication of the level of contaminant. In one arrangement the barrier comprises a plurality of generally radial elements, the barrier being rotatably mounted so as to bring successive elements into the fluid path on rotation.

BRIEF DESCRIPTION OF THE DRAWINGS

The invention may be performed in various ways, and specific examples will now be described, with reference to the accompanying drawings, in which.

DETAILED DESCRIPTION OF THE DRAWINGS

The invention recognizes that the degree of contamination of a fluid by undissolved particles is usually represented by the number or mass of these particles in a unit volume of the liquid. Therefore an indication of contamination could be obtained by extracting the particles from a known volume of the fluid. However, the measurement of the number or mass of particles removed is extremely time consuming using conventional methods. In the embodiments described below the quantity of particles is determined by the fact that the barrier blocks at a known rate for a given contamination level. Thus if a known quantity of fluid containing contaminant is passed through the barrier, then the degree of blockage of the barrier will give an indication of the amount of contaminant within the fluid.

Figure 1:
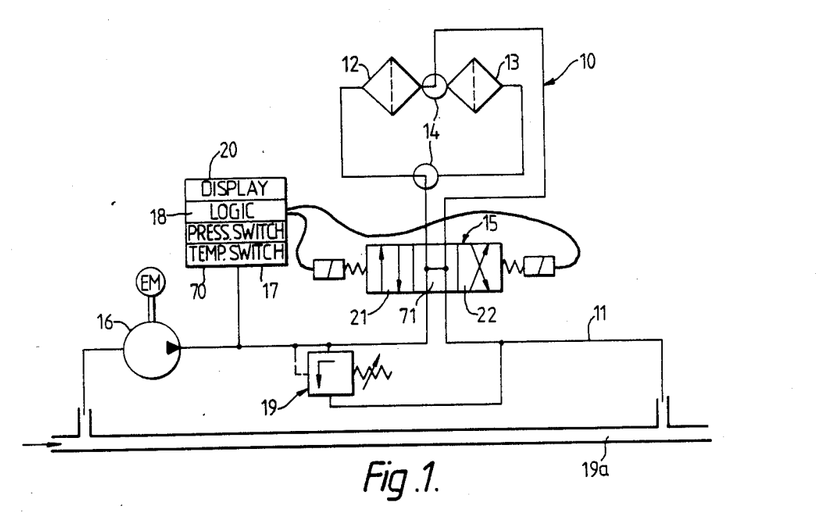
FIG. 1 is a diagrammatic circuit of a contamination indicator according to the invention.

Referring to FIG. 1, a contamination indicator is generally shown at 10. The indicator 10 includes a bypass 11 into which barriers 12, 13 can be introduced by means of two 3-way valves 14. The direction of flow, through whichever of the barriers 12, 13 is connected into the bypass 11, is controlled by a slide valve 15. The bypass 11 includes flow rate control means in the form of a constant flow pump 16 and pressure sensing means in the form of a pressure detector 17 disposed between the pump 16 and slide valve 15. The detector 17 controls the operation of the slide valve 15 through a logic circuit 18. A pressure release valve 19 is provided in the bypass 11.

The bypass 11 is connected in parallel with a part 19a of a fluid system, for example an hydraulic system. When the pump 16 is turned on it draws a continuous sample of fluid from the hydraulic line 19a and passes it, at a constant flow rate, through whichever of the barriers 12 or 13 is connected in the circuit. If the fluid is contaminated the particles will progressively block the barrier until the pressure upstream of the barrier has increased to the preset level of the pressure detector 17.

The logic circuit 18 includes a timer (not shown) for measuring the time taken between the beginning of the sampling of fluid when valve 15 moves to a sampling position 21 or 22, and the moment of reaching the preset level of the pressure detector. As fluid flows to the barrier at a constant rate, the time taken to block the barrier is a direct indication of the quantity of contaminant in the fluid of a size greater than the pore size of the barrier employed.

Obviously any one sample taken from the fluid may be unrepresentative of the contamination level throughout the fluid and it is therefore preferred to take a series of time readings to obtain a mean, which can be displayed at 20. This can be achieved by use of the slide valve 15. When the sampling cycle commences, the logic circuit 18 moves the slide valve so that the barrier 12 or 13 is connected into the bypass 11 by means of the left-hand valve portion 21 causing the fluid to flow, for example, from left to right through the fine barrier 12. When the barrier becomes blocked no further measurements can be taken until it is cleared. Therefore, in response to the detection of an increase in pressure, the slide valve 15 is moved under control of the logic circuit 18 so that its right-hand portion 22 connects the barrier 12 into the bypass 11 giving a flow through the barrier from right to left. This has the effect of back flushing the barrier and at the same time allowing a further measurement cycle to begin. At the end of that cycle the slide valve 15 is moved so that its left-hand side 21 is again in the circuit. Conveniently each cycle may take 1 to 60 seconds and a mean reading may be displayed typically every 10 cycles. However, a continuous reading could of course be given. It will be observed that the arrangement of the slide valve 15 is such that the flow of fluid through the bypass 11 is always in the same direction.

The pressure of fluid sensed by the pressure detector 17 will be directly proportional to the viscosity of the fluid. Hence if a fluid having a much greater viscosity is passed through the apparatus of FIG. 1, it may be that the pressure of fluid upstream of a completely unblocked barrier is already close to or even greater than the pre-set level of the pressure detector 17. The pre-set level of the detector 17 should therefore be adjusted if fluids of differing viscosities are to be sampled by the apparatus so that measurement cycles of between 1 and 60 second are still obtained.

The viscosity of a fluid to be sampled is also temperature dependent. The viscosity of a working fluid may be an order of magnitude greater when cold on start up of the system compared to its normal operating temperature. There is therefore additionally provided a temperature detector 70 to detect the temperature of fluid in the bypass 11. Whenever the temperature of the fluid is below a preset level the logic circuit 18 holds the slide valve 15 in the open center position 71 causing circulation of the fluid without sampling through the barriers 12 or 13. It is only when the temperature reaches an acceptable level that the detector 70 switches the slide valve 15 to position 21 to allow flow through the barrier. The detector 70 will be preset to switch the slide valve 15 when the temperature of the fluid rises to a level where its viscosity is not so critically temperature dependent, typically above 30° C. or even 40° C.

The extent of the blockage of the barrier can be determined from a knowledge of the pressure drop across the barrier when new, $\Delta P_o$ and the pressure drop after a time t, $\Delta P_t$. The greater the quantity of contaminant being trapped the greater $\Delta P_t$ will be in the given time, t. A determination of the blockage can be made by calculating the proportion of open area left in the barrier from an examination of $\Delta P_o$ and $\Delta P_t$. Thus when $\Delta P_o/\Delta P_t = 1$ the barrier is fully open (clean) but when $\Delta P_o/\Delta P_t = 0$ the open area is zero and the barrier is fully blocked. The apparatus can be used to give a general indication of contaminant level, by the provision of monitoring means which can determine simply whether the time taken to reach a predetermined pressure or flow rate falls within one predetermined range or another.

Alternatively the apparatus can be used as a particle counter. Knowing the consistency of the pore size, the total number of pores may be evaluated. If this is known, together with the flow rate and the $\Delta P_o/\Delta P_t$ for a time t then the total number of particles larger than the pore size per unit volume can be calculated.

Instead of switching the slide valve 15 whenever the barrier becomes blocked, it is possible to obtain an indication of contaminant level by measuring the pressure upstream of the barrier after the elapse of a predetermined cycle time and switching the valve at the end of each cycle.

Normally the fine barrier will be used, but a coarse barrier 13 is provided for initial use when it is suspected that there may be a very high level of contamination or that the particulate size of the contamination is large or some indication of the particulate size distribution is required. The logic circuit 18 may weight the obtained indication before display, according to which barrier is in the circuit.

Figure 2:
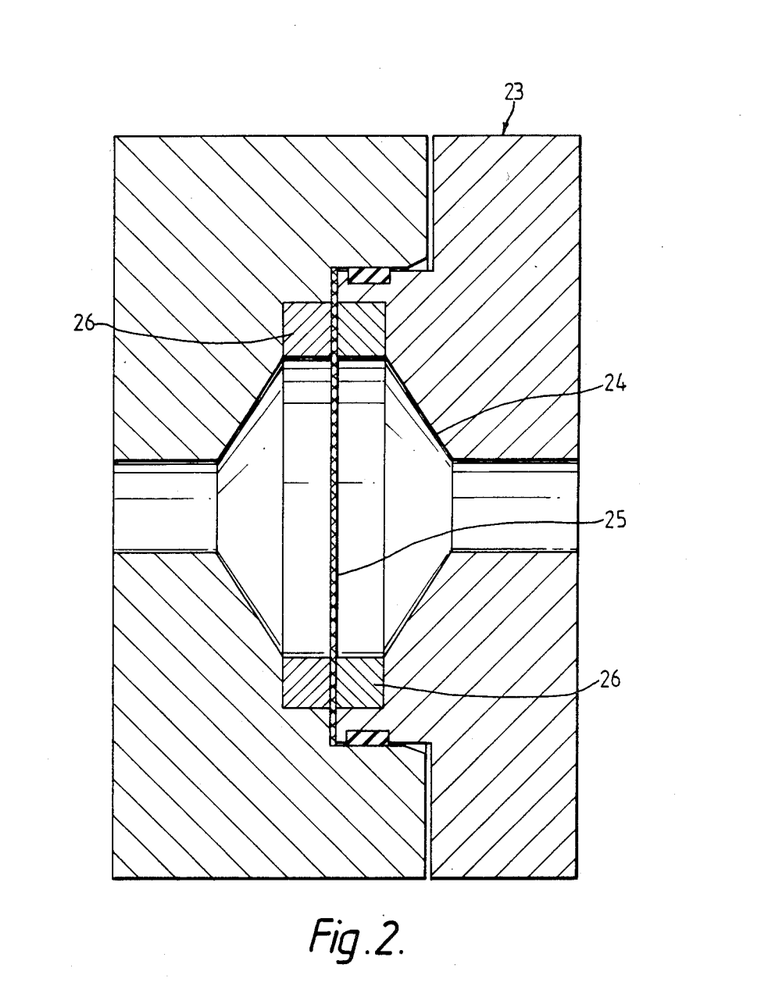
FIG. 2 is a sectional view of a filter holder for use with the indicator of FIG. 1.

FIG. 2 shows a holder 23 for the barrier material, which is preferably in the form of a woven metal mesh such as Dutch weave wire cloth mesh or Beta mesh, although it may be formed by any suitable pervious material. It will be appreciated that the pore size of the barrier is dependent, to some extent on the likely contaminant level in the fluid, but it has been found that a pore size within the range of 5 to 25 microns is generally most suitable for use with hydraulic fluid and in particular 16 microns has been found to be an acceptable pore size.

It is desirable that the fluid flows equally through the whole of the effective area of the barrier and for this reason the barrier holder 23 may be formed with an enlarged chamber 24 across which the barrier 25 extends. Alternatively the barrier holder may have a similar cross-sectional area to the inlet pipe. It is preferred that the barrier 25 is gripped tightly around its periphery, to limit flexing of the barrier on flow reversal, so that fatigue does not greatly shorten the barrier life. Alternatively the gripping rings 26 may provide added support by means of spokes or an additional coarse barrier. However, in some instances flexing of the barrier on reversal may provide a useful freeing action to assist back-flush of the contaminant.

Figure 3:
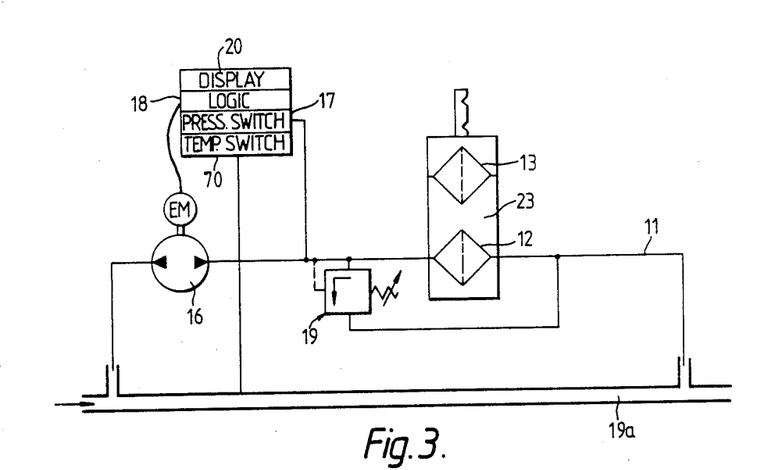
FIG. 3 is an alternative embodiment of an indicator according to the invention.

FIG. 3 shows an alternative contamination indicator, which works on the same basic principle as that of FIG. 1, but provides indications of the contaminant level only when the fluid is flowing from left to right through the barrier 12 or 13. In between each measurement cycle the pump 16 is reversed to provide back flush flow for a preset time. It will be seen that the fine and coarse barriers 12, 13 are mounted in a single holder 23 which can be moved laterally with respect to the bypass 11 to allow barrier selection. Temperature detector 70 ensures, via logic circuit 18, that pump 16 is actuated only when the fluid in the main flow line 19a reaches a predetermined minimum temperature.

It will be appreciated that instead of maintaining a constant flow to the barrier and measuring the pressure it is equally possible to maintain constant the pressure supplied to the barrier and to monitor the flow rate. An indication can then be obtained either when the flow rate drops below a predetermined level or by measuring the flow rate after a predetermined measurement time.

Figure 4:
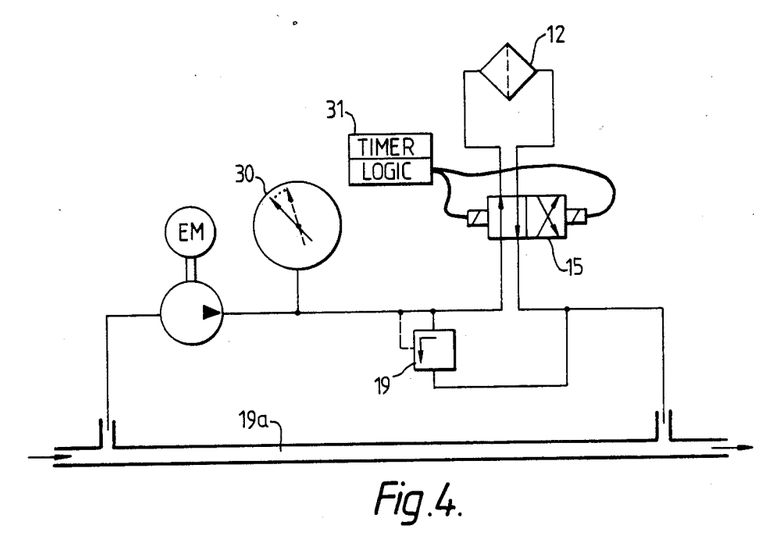
FIG. 4 is another alternative embodiment of an indicator according to the invention.

FIG. 4 illustrates a further embodiment of the invention, intended to give an easily readable, general indication of the level of contaminant in flow line 19a. A slide valve 15 is controlled by a timer 31 (including a logic circuit), such that fluid is passed through barrier 12 for a known predetermined time, typically for a 16 micron barrier, 60 seconds. The build up of pressure upstream of the barrier 12 is displayed by a pressure gauge 30. The increase in pressure displayed by gauge 30 gives a general indication of the degree of contamination in the fluid. After the predetermined time period, the slide valve 15 is actuated under the control of the logic circuit to reverse the direction of fluid flow through the barrier 12.

Figure 5:
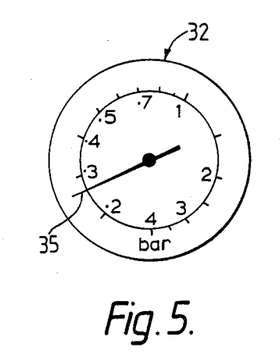
FIG. 5 is a detailed view of the pressure gauge of FIG. 4.

FIG. 5 illustrates a logarithmic pressure gauge for use with the apparatus of FIG. 4. A logarithmic pressure gauge has the advantage that, for a rise in pressure from $P_o$ to $P_t$, a ratio $P_t/P_o$ will be represented by a constant angular displacement of the needle 35 whatever the value of the particular starting pressure $P_o$. In the particular example illustrated in FIG. 5 the face 32 of the gauge is such that $P_t/P_o=2$ (ie a doubling of the starting pressure $P_o$) is represented by an angular displacement of approximately 75°.

Figure 6:
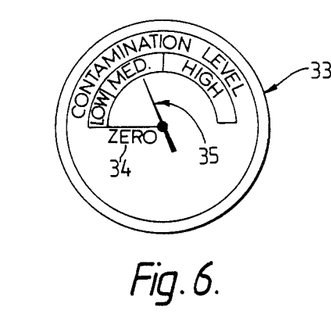
FIG. 6 is an illustration of an overlay scale for the gauge of FIG. 5.

To facilitate easy interpretation of the contamination reading there may be provided a rotatable overlay scale as shown at 33 in FIG. 6. In use the scale is rotated so that a zero line 34 is aligned with the needle position ($P_o$) at the start of a cycle. At the end of a cycle the position of the needle 35 ($P_t$) will indicate the severity of the contamination in the fluid. The cycle then recommences and the needle will oscillate with a period governed by the timer 31. Should the viscosity of the fluid change all that is required is to reset the zero line 34 at the new $P_o$ by rotation of the overlay scale 33. Should the pressure rise an amount to exceed the gauge value the relief valve 19 will open.

Figure 7:
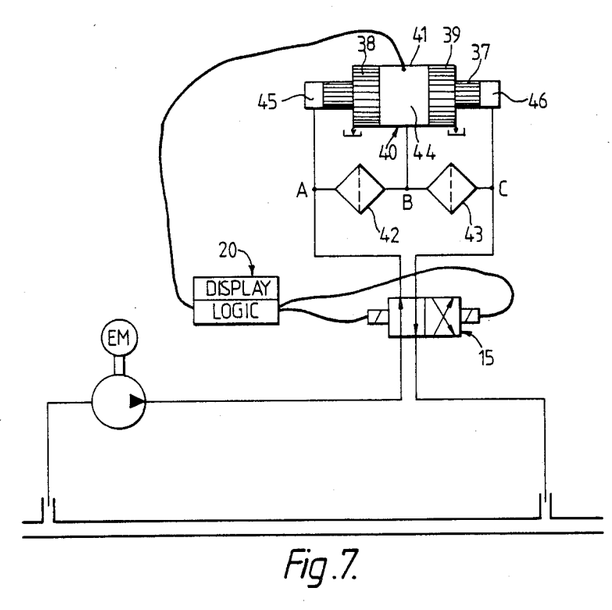
FIG. 7 shows yet another embodiment of an indicator according to the invention.

Another alternative embodiment of the invention is illustrated in FIG. 7. In this embodiment there are provided two similar barriers 42 and 43 connected in series. Also provided is a cylinder 40 within which are reciprocable two pistons 38 and 39. The line upstream of barrier 42 at A communicates with space 45 at one end of the cylinder while the line downstream of barrier 43 at C communicates with space 46 at the opposite end of the cylinder. The line between the two barriers 42 and 43 at B communicates with a space 44 between the two pistons 38 and 39.

The two barriers are similar and hence when unblocked the pressure drop across each barrier will be similar. However, in operation barrier 42 will begin to block but barrier 43 will remain unblocked as the pore sizes of the two barriers are similar and the fluid will have been prefiltered by barrier 42. Hence, if $P_A$, $P_B$, $P_C$ are the pressures at A, B and C respectively, $P_A$ will rise but $P_B$ will remain relatively constant. $P_A$ will eventually reach a pressure where the piston 38 will be moved towards the center of the cylinder 40, actuating a trip switch 41 which causes the slide valve 15 to reverse the direction of flow of fluid. With the flow reversed barrier 43 will begin to block and barrier 42 will be flushed clean. $P_A$ will now be small and piston 38 will return to its original position. As barrier 43 becomes progressively blocked, $P_C$ will rise and piston 39 will move towards the centre to actuate the trip switch 41 and reverse the flow once again. An indication of the level of contaminant in the fluid can be gained from the period of the measurement cycle, a high level of contaminant causing a relatively short cycle period and vice versa.

The measurement is independent of the viscosity of the fluid as it is the pressure ratio $P_t/P_o$ across a barrier which causes a piston to move rather than a measurement of a pressure value $P_t$. The pressure ratio required to effect movement of a piston is governed solely by the relative areas of the front and rear faces of that piston.

Figure 8:
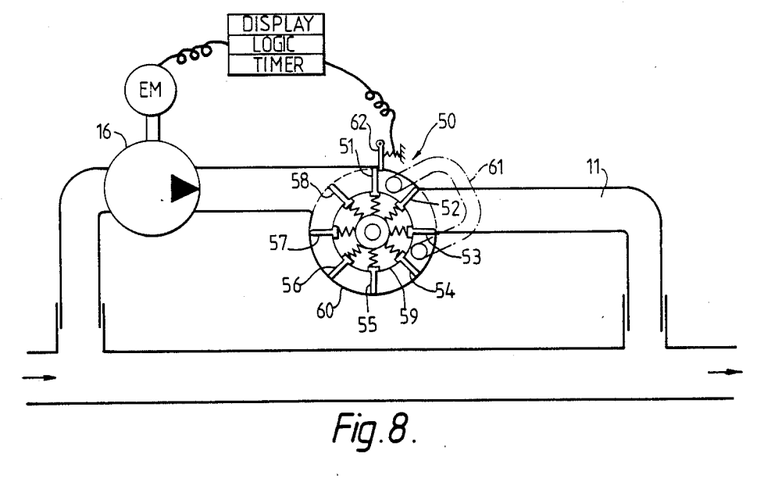
FIG. 8 shows a further embodiment of the invention, incorporating a movable barrier assembly.

FIG. 8 shows a further embodiment of the invention, which includes a movable barrier construction in the form of a rotary assembly generally indicated at 50. Eight radial vanes, 51 to 58, are shown installed in a drum 59 which is free to rotate. The vanes are spring loaded in a radial direction to urge them in to contact with a casing 60: alternate vanes are solid barriers (such as 52, 54 etc) or previous barriers (51, 53 etc) of the same or different porosity.

A main bypass 11 itself has a short bypass 61 which, in the position shown, connects the gap between vanes 51 and 52 with the gap between vanes 53 and 54. A latching device 62 is fitted to restrain the drum 59 from rotation until a predetermined pressure drop across barrier 51 is reached.

When the pump 16 is turned on a constant flow passes through the pervious barrier 51, through the bypass 61, through the pervious barrier 53 and out through the main bypass 11.

When the pervious barrier 51 begins to block with contaminant the pressure across the barrier 51 builds up until it is such that it overcomes the resistance of the latching device 62 and the drum rotates due to the flow.

The solid barrier 58 now blocks the flow and the pressure drop builds up rapidly causing the drum to continue rotation until the next pervious barrier is in position. Pervious barrier 57 now takes the flow and begins to block. At the same time flow through the bypass 61 back flushes the contaminated barrier 51.

The rotary movement of the drum 59 on its axis in a given time provides an indication of the level of contaminant in the fluid. In addition, if pervious barriers of four different porosities are used, the level of contamination at each of the four sizes can be assessed in any one rotation.

The indicators described above can be either permanently connected to a fluid system or they can be in the form of a portable instrument which can be connected, by valves, to any system, when it is desired to obtain an indication of contamination. Particularly in the portable form, it may be convenient to include a bleed valve in the bypass 11 whereby the system could be flushed before any measurements are taken.

The indicators can be used with a variety of fluid systems, for example, hydraulic, lubrication, fuel or air systems.

As an alternative to providing a facility for reversing the flow through the barrier 25, a plurality of barriers on a carousel or other moveable frame or paper strip can be used. In this case a new barrier would be introduced after each measurement cycle; the dirty barriers being cleaned externally to the bypass, before reintroduction into the system. Alternatively the barrier, rather than the flow, could be reversed at the end of each measurement cycle.

The embodiments of the invention described heretofore monitor the rate of blocking of the barrier by sensing the rise in pressure upstream of the barrier. However if the fluid system is such that the pressure of fluid downstream of the barrier is likely to vary, it may be desirable to measure the pressure both upstream and downstream to determine the pressure drop across the barrier. Such variants are well known by those skilled in the art and will be recognized as falling within the scope of the present invention.

We claim:

1. An apparatus for providing a continuous indication of a level of contaminant in a fluid comprising:
    a working fluid system;
    a by-pass connected to said working fluid system;
    flow rate control means in said by-pass whereby fluid flow through said by-pass can be controlled;
    a pervious barrier in said by-pass, said barrier having pores of a known size therein;
    a slide valve in said by-pass wherein fluid flow through said by-pass can be directed to one of a first or second sides of said barrier; and
    a logic circuit responsive to pressure upstream of said barrier and to time whereby a rate of build-up of contaminant of particle size greater than said known size of said pores can be measured;
    said logic circuit being operatively connected to said slide valve such that at a predetermined criterion said slide valve is actuated to redirect fluid flow to the other side of said barrier whereby contaminant is back flushed from said barrier whereafter another measurement is commenced,
    said logic circuit being adapted to process said rate of build-up and to average said rate of build-up over a plurality of cycles to provide an indication of the level of contaminant in said fluid,
    said logic circuit comprising means for compensating for variations in the viscosity of the fluid, the compensating means comprising means for obtaining, at different times, first and second values representative of a variable quantity, and means for deriving a ratio of said first and second values, the variable quantity being a function of the fluid flow rate through the barrier and the pressure drop across the barrier.

2. Apparatus according to claim 1 wherein said flow rate control means is a pump.

3. Apparatus according to claim 1 wherein said predetermined criterion is a period of time.

4. Apparatus according to claim 1 wherein said predetermined criterion is a pressure level.

5. Apparatus according to claim 1 wherein said logic circuit includes pressure rate sensing means for sensing measurements representing the rate at which the pressure of the fluid upstream of the barrier rises and also timing means.

6. Apparatus according to claim 1 wherein the barrier is in the form of a woven mesh.

7. Apparatus according to claim 6 wherein the barrier is in the form of a woven wire mesh.

8. Apparatus according to claim 6 wherein the barrier is of Dutch weave wire cloth mesh, or Beta mesh.

9. Apparatus according to claim 1 wherein said logic circuit further comprises flow rate control means adapted to maintain constant the flow of fluid supplied to the barrier.

10. Apparatus according to claim 1 wherein the viscosity compensating means comprises a logarithmic pressure gauge for sensing first and second values of the fluid pressure drop across the barrier.

11. Apparatus according to claim 10 wherein the logarithmic pressure gauge is provided with an adjustable overlay scale.

12. Apparatus according to claim 1 wherein the viscosity compensating means comprises a stepped piston movable longitudinally within a stepped cylinder, the piston having a large face which can be exposed to fluid at a first pressure representative of the pressure drop across the barrier when in a relatively unblocked condition, and having a smaller face which can be exposed to fluid at a second pressure representative of the pressure drop across the barrier after a quantity of the fluid has flowed therethrough.

13. Apparatus according to claim 12 wherein an indication of the level of contaminant is provided in response to movement of the stepped piston under the influence of the differential pressures applied to its faces.

14. Apparatus according to claim 12 wherein there are provided two similar barriers connected in series; two stepped pistons whose larger faces can be exposed to the fluid pressure prevailing at a point between the two barriers, and whose smaller faces can be exposed one to the pressure prevailing upstream of the barrier and the other to the pressure prevailing downstream of the barrier; and means for reversing the direction of fluid flow through the barriers in response to the provision of an indication.

* * * * *

UNITED STATES PATENT AND TRADEMARK OFFICE
CERTIFICATE OF CORRECTION

PATENT NO. : 4,583,396
DATED : April 22, 1986
INVENTOR(S) : Hunt, et al.

It is certified that error appears in the above-identified patent and that said Letters Patent is hereby corrected as shown below:

On the title page assignee should read

--(73) Assignee: Secretary of The State For Defence In Her Majest's Government of the United Kingdom of Great Britain and Northern Ireland, The Whitehall, London, England --.

Signed and Sealed this

Fourteenth Day of October, 1986

[SEAL]

*Attest:*

DONALD J. QUIGG

*Attesting Officer*  *Commissioner of Patents and Trademarks*